United States Patent [19]

Hillstead

[11] Patent Number: 4,921,484
[45] Date of Patent: May 1, 1990

[54] MESH BALLOON CATHETER DEVICE

[75] Inventor: Richard A. Hillstead, Hollywood, Fla.

[73] Assignee: Cordis Corporation, Miami Lakes (Hialeah), Fla.

[21] Appl. No.: 223,870

[22] Filed: Jul. 25, 1988

[51] Int. Cl.⁵ .......................................... A61M 25/00
[52] U.S. Cl. ................................ 604/104; 606/194; 606/159
[58] Field of Search ........................... 604/104–107, 604/95, 96, 22, 268; 128/341–344, 325

[56] References Cited

U.S. PATENT DOCUMENTS

| | | | |
|---|---|---|---|
| 2,498,692 | 2/1950 | Mains | 128/348 |
| 2,816,552 | 12/1957 | Hoffman | 128/305 |
| 3,416,531 | 12/1968 | Edwards | 128/348 |
| 3,433,226 | 3/1969 | Boyd | 128/305 |
| 3,495,586 | 2/1970 | Regenbogen | 128/6 |
| 3,568,659 | 3/1971 | Karnegia | 128/1 |
| 3,605,725 | 9/1971 | Bentov | 128/2.05 R |
| 3,623,483 | 11/1971 | Dyer, Jr. | 128/276 |
| 3,692,029 | 9/1972 | Adair | 128/349 R |
| 3,713,447 | 1/1973 | Adair | 128/347 |
| 3,773,034 | 11/1973 | Burns et al. | 128/2 M |
| 3,868,956 | 3/1975 | Alfidi et al. | 128/345 |
| 3,938,530 | 2/1976 | Santomieri | 128/349 R |
| 3,996,938 | 12/1976 | Clark | 128/348 |
| 4,043,338 | 8/1977 | Homm et al. | 128/260 |
| 4,154,242 | 5/1979 | Termanini | 128/349 R |
| 4,522,195 | 7/1985 | Schiff | 128/1 D |
| 4,535,757 | 8/1985 | Webster, Jr. | 128/1 D |
| 4,572,186 | 2/1986 | Gould et al. | 128/341 |
| 4,577,631 | 3/1986 | Kreamer | 128/334 R |
| 4,607,618 | 8/1986 | Angelchik | 128/1 R |
| 4,608,965 | 9/1986 | Anspach, Jr. et al. | 128/4 |
| 4,650,466 | 3/1987 | Luther | 604/95 |
| 4,655,745 | 4/1987 | Corbett | 604/49 |
| 4,655,748 | 4/1987 | Mushika | 604/96 |
| 4,655,771 | 4/1987 | Wallsten | 128/343 |
| 4,693,243 | 9/1987 | Buras | 128/207 |
| 4,706,670 | 11/1987 | Andersen et al. | 128/344 |

Primary Examiner—Stephen C. Pellegrino
Attorney, Agent, or Firm—Henry W. Collins; Thomas R. Vigil

[57] ABSTRACT

The mesh balloon catheter device includes a catheter having a distal end and a proximal end, a tube of woven interlaced filaments forming a tubular mesh and having a proximal end connected to the distal end of the catheter and a distal end, a flush tube or fiber optic tube extending through the catheter and the tubular mesh and fixed to the distal end of the tubular mesh, and a mechanism for moving the distal end of the tubular mesh toward the proximal end of the tubular mesh to cause the tubular mesh to balloon laterally outwardly to the shape of a mesh balloon.

The moving mechanism can be realized by the flush tube or fiber optic tube connected to the distal end of the tubular mesh or by a control wire connected to the distal end of the tubular mesh and extending through the catheter.

14 Claims, 2 Drawing Sheets

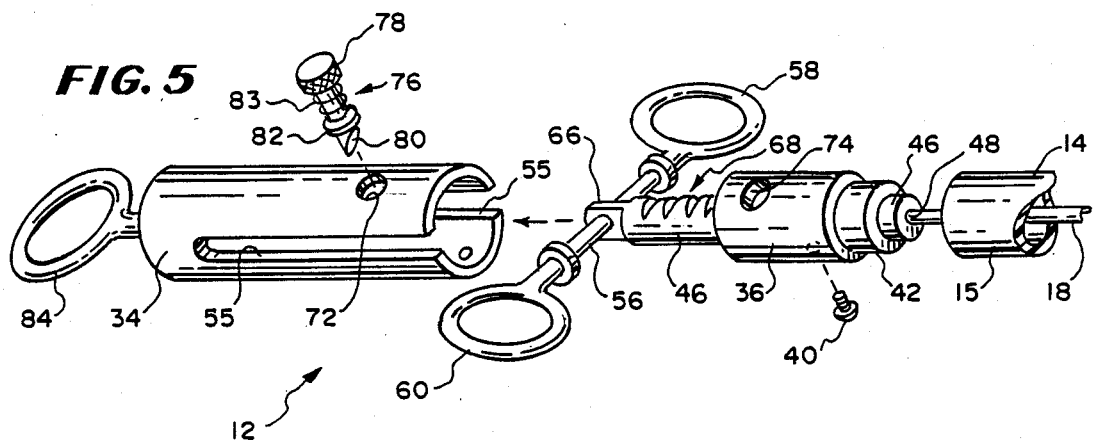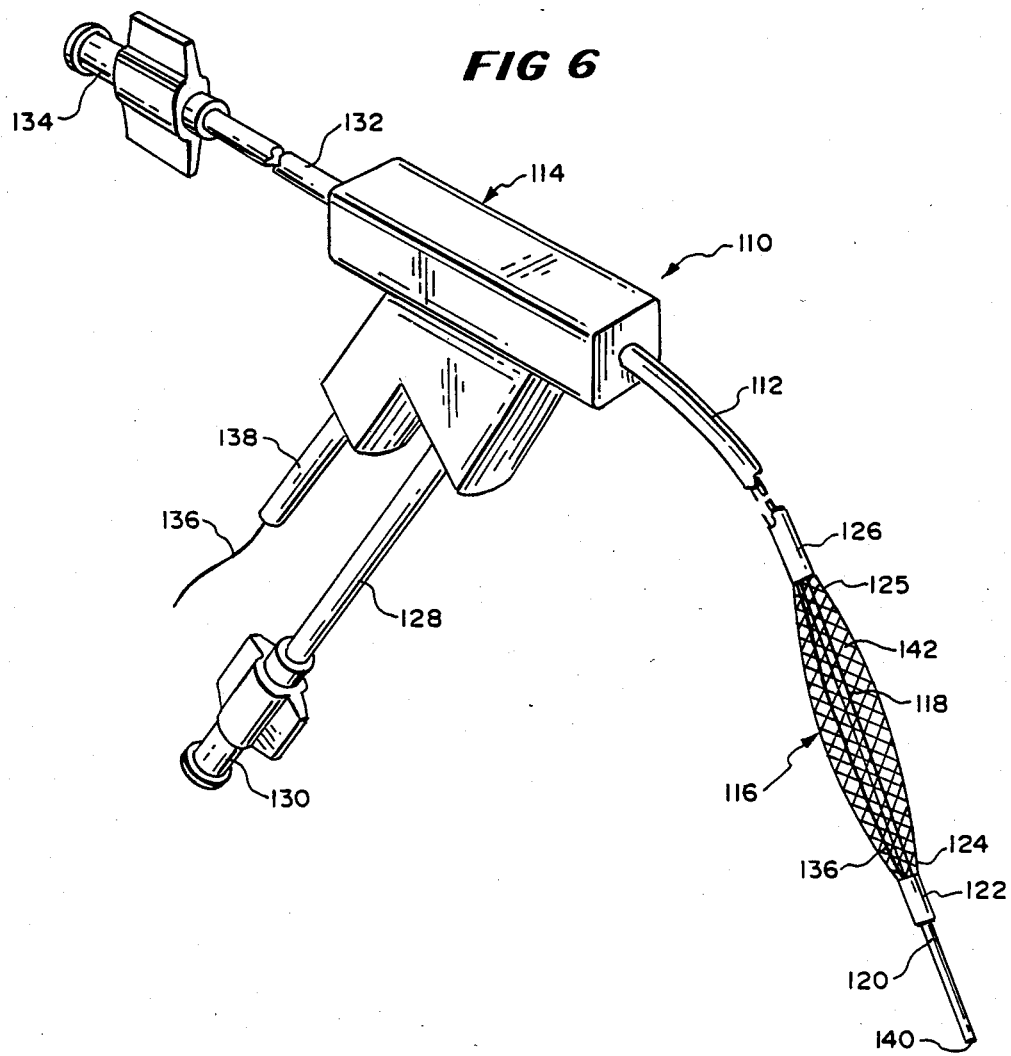

MESH BALLOON CATHETER DEVICE

BACKGROUND OF THE INVENTION

1. Field of the Invention

The present invention relates to a mesh balloon catheter device which can be referred to as an angioplasty device for removing and/or compressing the buildup of material in a vessel, such as the buildup of plaque in an area of stenosis in a vessel. The mesh balloon catheter device can also be used in other cavities and vessels of the body for distention of the area upon actuation of the mesh balloon device to create a mesh balloon in the area to be distended.

2. Description of the Prior Art

Heretofore it has been proposed to provide an angioplasty device having a flexible woven tube which can be contracted axially to cause the woven tube to balloon outwardly to form a mesh balloon in the Luther U.S. Pat. No. 4,650,466.

The Luther patent teaches the construction of such an angioplasty device in the form of a woven tube of tubular fabric mounted forwardly of a catheter and having a guidewire arrangement for retracting the distal end of the tubular fabric relative to the proximal end thereof. The woven tube may be lined with a filter cloth of nylon or polyester which expands with the woven tube for collecting particles and debris and for removing same from a vessel.

As will be described in greater detail hereinafter, the mesh balloon catheter device of the present invention differs from the angioplasty device disclosed in the Luther patent by providing a central tube within the mesh balloon catheter device having a forward end which extends to the distal end of a tubular mesh and through which fluid can be injected or withdrawn from the area adjacent the tubular mesh or adjacent a mesh balloon formed therewith when the distal end of the tubular mesh is contracted toward the proximal end thereof.

SUMMARY OF THE INVENTION

According to the invention there is provided a mesh balloon catheter device comprising:

a catheter having a distal end and a proximal end;

a tube of woven interlaced filaments forming a tubular mesh and having a proximal end connected to the distal end of said catheter and a distal end;

a flush tube extending through said catheter and said tubular mesh and fixed to the distal end of said tubular mesh;

means located within said catheter and connected to said distal end of said tubular mesh for moving said distal end of said tubular mesh toward said proximal end of said tubular mesh to cause said tubular mesh to balloon laterally outwardly to the shape of a mesh balloon; and a fluid coupling from said tubular mesh to the proximal end of said catheter for draining fluid from the catheter which may have entered the catheter through said tubular mesh.

Also according to the invention there is provided a mesh balloon catheter device comprising:

a catheter having a distal end and a proximal end;

a tube of woven interlaced filaments forming a tubular mesh and having a proximal end connected to the distal end of said catheter and a distal end;

a flush tube extending through said catheter and said tubular mesh and fixed to the distal end of said tubular mesh;

means located within said catheter and connected to said distal end of said tubular mesh for moving said distal end of said tubular mesh toward said proximal end of said tubular mesh to cause said tubular mesh to balloon laterally outwardly to the shape of a mesh balloon;

actuating means coupled to the proximal end of said catheter and being connected to said means for moving said distal end of said tubular mesh; and, said actuating means includes means for indexing said moving means in predetermined increments rearwardly from said proximal end of said catheter where by an operator of said device may know how much said tubular has been contracted to create a mesh balloon.

Further according to the invention there is provided a mesh balloon catheter device comprising:

a catheter having a distal end and a proximal end;

a tube of woven interlaced filaments forming a tubular mesh and having a proximal end connected to the distal end of said catheter and a distal end;

a flush tube extending through said catheter and said tubular mesh and fixed to the distal end of said tubular mesh;

a fitting coupled to the proximal end of said catheter, said fitting including a tubular outlet that is coupled within said fitting to said flush tube;

a drainage tubing extending proximally from said fitting and coupled within said fitting to said catheter for draining fluid from the area of the tubular mesh;

a control wire within said catheter connected to the distal end of said tubular mesh and extending through said tubular mesh, said catheter and said fitting and out of an outlet tube of said fitting, to a proximal end of said control wire;

and said control wire being movable rearwardly to expand said tubular mesh into a mesh balloon.

Still further according to the invention there is provided a mesh balloon catheter device comprising:

a catheter having a distal end and a proximal end;

a tube of woven interlaced filaments forming a tubular mesh and having a proximal end connected to the distal end of said catheter and a distal end;

a fiber optic tubing extending through said catheter and said tubular mesh and fixed to the distal end of said tubular mesh; and means for moving said distal end of said tubular mesh toward said proximal end of said tubular mesh to cause said tubular mesh to balloon laterally outwardly to the shape of a mesh balloon.

BRIEF DESCRIPTION OF THE DRAWINGS

FIG. 5 is an exploded perspective view of the actuating handle mechanism of the mesh balloon catheter device shown in FIG. 1.

FIG. 6 is a perspective view of a modified embodiment of the mesh balloon catheter device shown in FIGS. 1-5.

DESCRIPTION OF THE DRAWINGS

Figure 1:
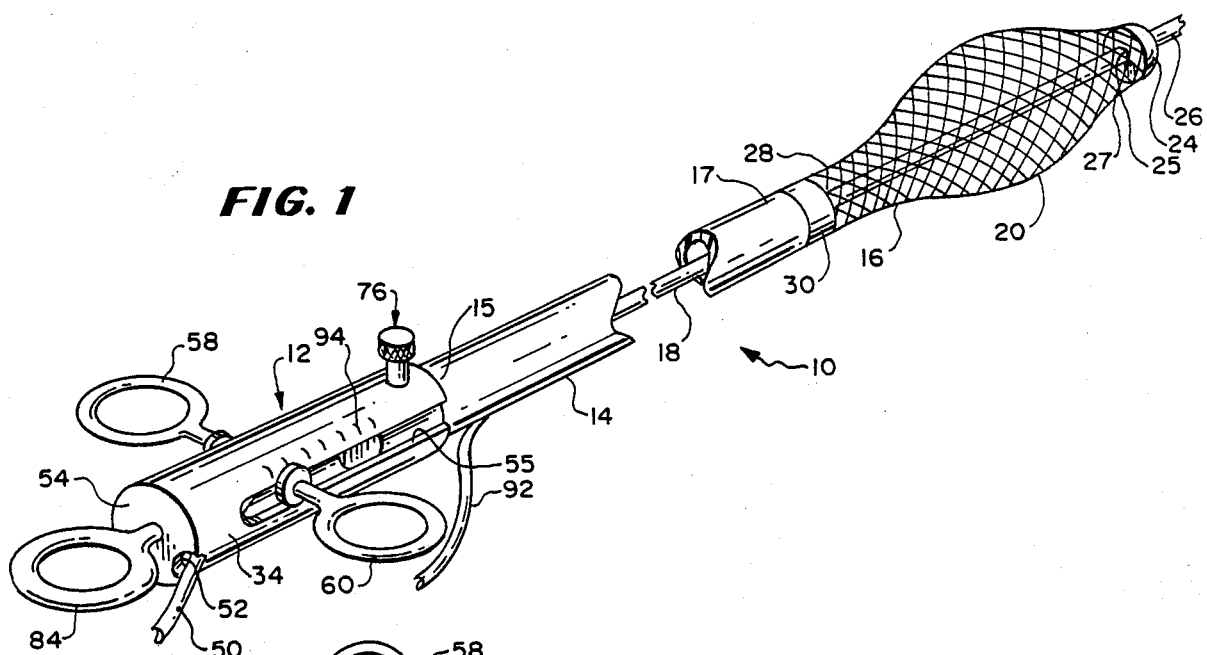
FIG. 1 is a perspective view with portions broken away of the mesh balloon catheter device of the present invention.

Referring to the drawings in greater detail, there is shown in FIG. 1 a mesh balloon catheter device 10 constructed according to the teachings of the present invention. The device 10 includes an actuating handle mechanism 12, an elongate catheter 14 which is shown broken away and is much longer than indicated in FIG. 1 and which has a proximal end 15 connected to the handle mechanism, and a tubular mesh 16 connected to a distal end 17 of the catheter 14. The tubular mesh 16 is woven of a tube of interlaced filaments of plastic, stainless steel, or other material woven into a "tubular mesh". Extending through the device 10 is a flush tube 18.

Figure 2:
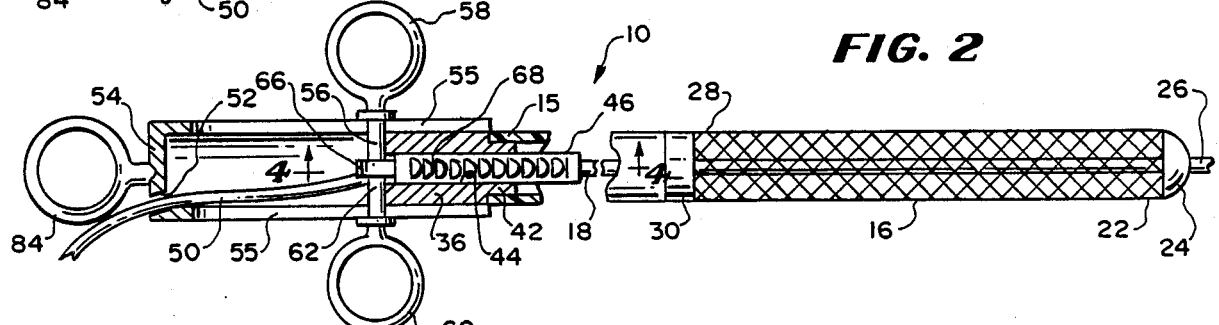
FIG. 2 is a longitudinal plan view of the mesh balloon catheter device shown in FIG. 1 with portions broken away.
Figure 3:
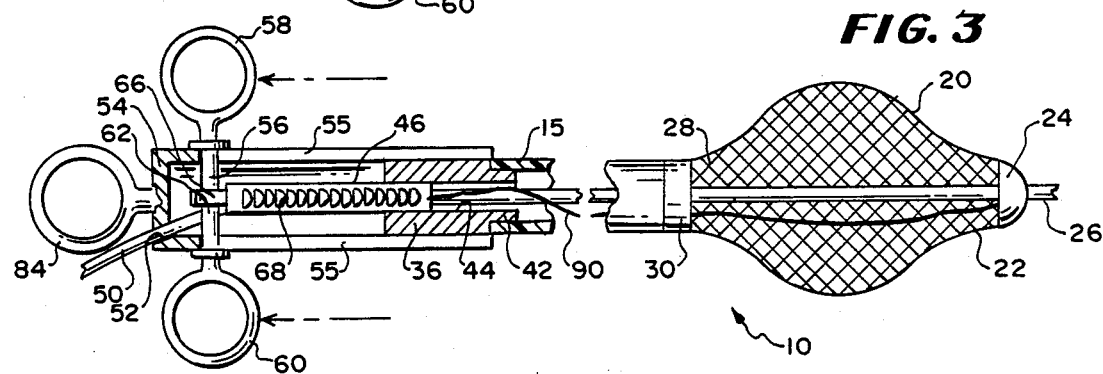
FIG. 3 is a longitudinal plan view of the mesh balloon catheter device shown in FIG. 2 with portions broken away and with a portion of an actuating handle mechanism of the device retracted to cause the tubular mesh to balloon out to form a mesh balloon.

The tubular mesh 16 is generally tubular in shape, as shown in FIG. 2, except when the device 10 is actuated to cause the tubular mesh 16 to balloon out to form a mesh balloon 20 (FIGS. 1 and 3).

At a distal end 22 of the tubular mesh 16 is a cap member 24 to which the distal end 22 of the tubular mesh 16 is fixed. This cap member 24 has a central hole 25 (FIG. 1) therethrough and a distal end portion 26 of the flush tubing 18 is received in this hole 25 and fixed therein. The distal end portion 26 of the flush tube 18 is shown extending beyond the cap member 24 and typically extends approximately one inch beyond the cap member 24. However, if desired, the flush tube 18 can end at the cap member 24, in which case flushing fluid would be ejected from the front of the cap member 24. 34 in which is received a sleeve 36 (FIGS. 2-4) which is fixed the cylinder 34, such as with a screw 40 shown in FIG. 4, and which has a reduced-in-diameter portion 42 which extends outwardly from the cylinder 34 and to which the proximal end 15 of the catheter 14 is attached. The sleeve 36 has a central bore 44 therethrough in which is received an actuating rod 46. The actuating rod 46 also has a central bore 48 (FIG. 4) through which the flush tube 18 extends. A portion 49 of the flush tube 18 is received in the bore 48 and can be fixed therein such as with an adhesive. The remaining portion 50 of the flush tube 18 extends out through a port 52 (FIGS. 2 and 3) in the rear end wall 54 of the cylinder 34.

The cylinder 34 has slots 55 on either side thereof extending from a position forward of the rear end wall 54 of the cylinder 34 toward the front of the cylinder 34. A transverse rod 56 (FIGS. 2 and 3) extends across the cylinder 34 and through the slots 55 and has opposed finger engaging side rings 58,60 fixed at either end thereof. A middle portion 62 of the transverse rod 56 is received through a transverse bore 64 (FIG. 4) at a proximal end 66 of the actuating rod 46 received in the center bore 44 of the sleeve 36.

Figure 4:
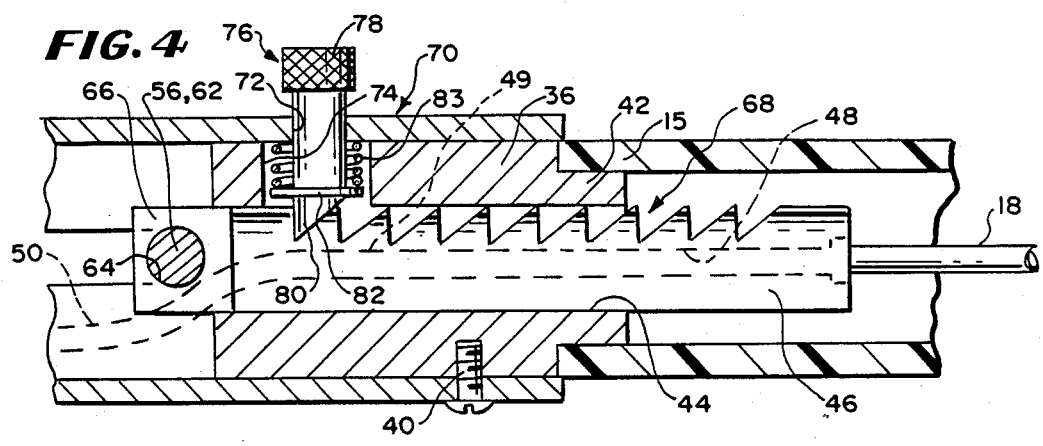
FIG. 4 is an enlarged fragmentary sectional view of a ratchet mechanism in the actuating handle mechanism of the mesh balloon catheter device shown in FIGS. 1, 2 and 3.

As best shown in FIG. 4, the rod 46 has formed on its upper side thereof a saw tooth ratchet formation 68. Then, as shown in FIG. 4, a top side 70 of the cylinder 34 has a hole 72 therein which is aligned with a mating hole 74 in the sleeve 36. Positioned in this hole 72 is a ratchet pin 76 having an upper knurled end 78 and a lower end 80 which is formed as a tooth 80. A washer 82 is located adjacent to and fixed to the lower tooth end 80. Between the washer 82 and the inner wall surface of the cylinder 34 is a spring 83 such that the ratchet pin 76 is spring biased downwardly to force the tooth 80 into one of the ratchet spaces in the saw tooth ratchet formation 68. An exploded view of the parts of the actuating handle mechanism 12 is shown in FIG. 5.

The rear end wall 54 of the cylinder 34 has a thumb receiving end ring 84 fixed thereto by which one can grasp the actuating handle mechanism 12 in one hand with the thumb being received in the end ring 84 and two of the fingers being received in the side rings 58,60 fixed to opposite ends of the transverse rod 56.

In use of the device 10, the catheter 14 is inserted into a body vessel, such as a blood vessel, and the tubular mesh 16 is positioned in a desired area in the vessel. Then, gripping the actuating handle mechanism 12, the side rings 58,60 are pulled rearwardly to pull the cap member 24 toward the collar 30. This is accomplished with the flush tube 18 fixed to the cap member 24, when it is also fixed to the actuating rod 46. Alternatively, this can be accomplished with a separate control wire 90, shown limp in FIG. 3, which can be connected between the cap member 24 and the actuating rod 46. When a separate control wire 90 is used, the portion 49 of the flush tube 18 is slidably received through the central bore 44 in the actuating rod 46.

Additionally, and as shown in FIG. 1, a drainage tube 92 can be connected to the proximal end 15 of the catheter 14 so that particles and fluid entering the mesh balloon 20 can drain out of the catheter 14.

The mesh balloon 20 can be extended in increments by means of the ratchet pin 76 moving in steps in the saw tooth ratchet formation 68. Indicia 94 (FIG. 1) can be provided for indicating the extent of rearward movement of the cap member 24 to indicate the amount of expansion of the mesh balloon 20.

A typical use of the device 10 is in an area of stenosis in a blood vessel where it is desired to expand the narrow passageway in a stenotic area. Flushing fluid can be inserted through flush tube 18 and plaque debris and fluid can be drained, evacuated or withdrawn through the catheter 14 and drainage tube 92.

In FIG. 6 is illustrated another embodiment of a balloon catheter device 110. In this embodiment, the device 110 includes a catheter 112 which extends between a Luer TM fitting 114 and a tubular mesh 116 which is expanded to form a mesh balloon. A flush tube 118 extends through the catheter 112 and the tubular mesh 116 and, of course, the catheter 112 is much longer than the length shown in FIG. 6 which is broken away to indicate that it is longer.

A distal end portion 120 of the flush tube 118 extends through a collar 122 and is fixed to the collar 122. Likewise, a distal end 124 of the tubular mesh 116 is fixed to the collar 122 and extends rearwardly to its proximal end 125 fixed to distal end 126 of the catheter 112.

The flush tube 118 extends slidably through the catheter 112 to the Luer TM fitting 114. In the Luer TM fitting 114, the flush tube 118 is connected to a side outlet tube 128 which has a coupling 130 thereon to which a source of flushing fluid can be coupled for supplying flushing fluid to the flush tube 118.

The catheter 112 is coupled within the Luer TM fitting 114 to an end outlet tube 132 having a coupling 134 thereon for connection to a drainage catheter not shown.

A control wire 136 connected to the collar 122 and extends through the catheter 112 to the Luer ™ fitting 114 and out a second side outlet tube 138 from the Luer ™ fitting 114, as shown. This control wire 136 can be connected to any suitable actuating mechanism, such as the actuating handle mechanism 12 used in the embodiment shown in FIGS. 1-5.

In this embodiment, the device 110 enables one to supply fluid to or remove fluid from the area within the tubular mesh 116 via the coupling 130 so that fluid can be introduced at an end 140 of the flush tube 118 or removed from end 140 of the flush tube 118. Then, expansion of the tubular mesh 116 to a mesh balloon shape is controlled by movement of the control wire 136. Since filaments or fibers 142 of the tubular mesh 116 are flexible and will resist flexing outwardly, the control wire 136 can be a pliable flexible wire, since only a pulling force needs to be exerted thereon to cause the tubular mesh 116 to balloon out to form a mesh balloon. Then when the control wire 136 is released, the resiliency of the filaments or fibers 142 of the tubular mesh 116 will cause it to resume the shape shown in FIG. 6.

From the foregoing description, it will be apparent that the mesh balloon catheter device 10 or 110 of the present invention has a number of advantages, some of which have been described above and others of which are inherent in the mesh balloon catheter device 10. For example, the device 10 can be used as a urinary catheter. The mesh balloon 20 can be expanded in the bladder to hold the catheter 14 or 112 in place while the mesh allows unobstructed urine flow.

The device 10 or 110 can be used as a biliary catheter. The mesh balloon 20 can be expanded in the bile tract to hold the catheter 14 or 112 in place for bile drainage.

The device 10 or 110 can be used as a stent placement. Two or more mesh balloons 20 can be placed in series for better stent placement in a body vessel or cavity.

The device 10 or 110 can be used as a dilation catheter. The mobility of the catheter 14 or 112 and the ease of expansion and contraction of the tubular mesh 18 or 116 with a simple "one hand" squeezing motion, gives a physician more control and flexibility during a dilation procedure.

The device 10 and 110 can be used as a filtration balloon mechanism. The mesh structure of the tubular mesh 18 or 116 is particularly attractive as a filtration deuce either in a drainage application or as a distal addition to a coronary angioplasty balloon catheter procedure.

Finally, the expandable tubular mesh can be used as a centering device for a laser catheter. For this use, the flush tube 18 or 116 is replaced with a fiber optic catheter. When directing laser radiation through such a fiber optic catheter, it is important that the laser emitting tip be centered in the occluded vessel. The expandable tubular mesh 18 or 116 lends itself quite nicely for this centering.

Also, it will be apparent that modifications can be made to the mesh balloon catheter of the present invention without department from the teachings thereof. Accordingly, the scope of the invention is only to be limited as necessitated by the accompanying claims.

I claim:

1. A mesh balloon catheter device comprising:
   a catheter having a distal end and a proximal end;
   a tube of woven interlaced filaments forming a tubular mesh and having a proximal end connected to the distal end of said catheter and a distal end;
   a flush tube extending through said catheter and said tubular mesh and fixed to the distal end of said tubular mesh;
   means located within said catheter and connected to said distal end of said tubular mesh for moving said distal end of said tubular mesh toward said proximal end of said tubular mesh to cause said tubular mesh to balloon laterally outwardly to the shape of a mesh balloon; and
   a fluid coupling from said tubular mesh to the proximal end of said catheter for draining fluid from the catheter which may have entered the catheter through said tubular mesh.

2. The device of claim 1 wherein said moving means includes said flush tube fixed to said distal end of said tubular mesh.

3. The device of claim 1 wherein said moving means includes a wire extending through said catheter and connected to said distal end of said tubular mesh.

4. The device of claim 1 further including a cap member fixed to the distal end of said tubular mesh and having an opening therethrough through which said flush tube extends with said flush tube being fixed to said cap.

5. The device of claim 4 having a portion of said flush tube extending beyond said cap.

6. The device of claim 1 having a portion of said flush tube extending beyond said distal end of said tubular mesh.

7. A mesh balloon catheter device comprising:
   a catheter having a distal end and a proximal end;
   a tube of woven interlaced filaments forming a tubular mesh and having a proximal end connected to the distal end of said catheter and a distal end;
   a flush tube extending through said catheter and said tubular mesh and fixed to the distal end of said tubular mesh;
   means located within said catheter and connected to said distal end of said tubular mesh for moving said distal end of said tubular mesh toward said proximal end of said tubular mesh to cause said tubular mesh to balloon outwardly to the shape of a mesh balloon;
   actuating means coupled to the proximal end of said catheter and being connected to said means for moving said distal end of said tubular mesh; and, said actuating means includes means for indexing said moving means in predetermined increments rearwardly from said proximal end of said catheter whereby an operator of said device may know how much said tubular has been contracted to create a mesh balloon.

8. The device of claim 7 wherein said actuating means includes a hollow cylinder having a rear end wall and an end ring extending from said end wall through which a thumb of an operator can be inserted, said means for indexing said moving means includes ratchet means comprising a ratchet member, a transverse rod connected to said ratchet member, and two side rings in which fingers of an operator can be inserted, said side rings being connected to opposite ends of said transverse rod.

9. The device of claim 8 wherein said flush tube extends through said ratchet means.

10. The device of claim 8 wherein said flush tube extends through and is fixed to said ratchet member of said ratchet means and comprise part of said moving means.

11. The device of claim 8 wherein said cylinder has a hole in the wall thereof, said ratchet means includes a ratchet pin resiliently mounted through said hole in said cylinder, said ratchet member having a saws tooth ratchet formation thereon, and said ratchet pin includes a spring biased tooth which is adapted to engage in said saw tooth ratchet formation on said ratchet member.

12. The device of claim 8 including indicia on said cylinder for indicating the extent of lateral expansion of said tubular mesh by reason of the position of one of said side rings relative to said indicia.

13. A mesh balloon catheter device comprising:
a catheter having a distal end and a proximal end;
a tube of woven interlaced filaments forming a tubular mesh and having a proximal end connected to the distal end of said catheter and a distal end;
a flush tube extending through said catheter and said tubular mesh and fixed to the distal end of said tubular mesh;
a fitting coupled to the proximal end of said catheter, said fitting including a tubular outlet that is coupled within said fitting to said flush tube;
a drainage tubing extending proximally from said fitting and coupled within said fitting to said catheter for draining fluid from the area of the tubular wire;
a control wire within said catheter connected to the distal end of said tubular mesh, said catheter and said fitting and out of an outlet tube of said fitting to a proximal end of said control wire;
and said control wire being movable rearwardly to expand said tubular mesh into a mesh balloon.

14. A mesh balloon catheter device comprising:
a catheter having a distal end and a proximal end;
a tube of woven interlaced filaments forming a tubular mesh and having a proximal end connected to the distal end of said catheter and a distal end;
a fiber optic tubing extending through said catheter and said tubular mesh and fixed to the distal end of said tubular mesh; and
means for moving said distal end of said tubular mesh toward said proximal end of said tubular mesh to cause said tubular mesh to balloon laterally outwardly to the shape of a mesh balloon.

* * * * *

UNITED STATES PATENT AND TRADEMARK OFFICE
CERTIFICATE OF CORRECTION

PATENT NO. : 4,921,484
DATED : May 1, 1990
INVENTOR(S) : Richard A. Hillstead It is certified that error appears in the above-identified patent and that said Letters Patent is hereby corrected as shown below:

Column 3, line 11 "DESCRIPTION OF THE DRAWINGS" should be --DESCRIPTION OF THE PREFERRED EMBODIMENT--.

Column 3, line 40 Between "cap member 24." and "34 in which" should be inserted the following paragraphs:
-- A proximal end 28 of the tubular mesh 16 is fixed to a collar 30 on a distal end 32 of the catheter 14. The flush tube 18 extends slidably through the collar 30 and through the catheter 14 to the actuating handle mechanism 12. The proximal end 15 of the catheter 14 is fixed to the mechanism 12 as shown.

The actuating handle mechanism includes a hollow cylinder--.

Signed and Sealed this

Sixth Day of April, 1993

*Attest:*

STEPHEN G. KUNIN

*Attesting Officer*     *Acting Commissioner of Patents and Trademarks*